United States Patent [19]

Zwicker

[11] 4,390,748
[45] Jun. 28, 1983

[54] ELECTRO-ACOUSTICAL MEASURING DEVICE AND METHOD

[75] Inventor: Eberhard Zwicker, Icking, Fed. Rep. of Germany

[73] Assignee: Siemens Aktiengesellschaft, Berlin & Munich, Fed. Rep. of Germany

[21] Appl. No.: 214,779

[22] Filed: Dec. 9, 1980

[30] Foreign Application Priority Data

Dec. 21, 1979 [DE]  Fed. Rep. of Germany ....... 2951856

[51] Int. Cl.³ ............................................... A61B 5/12
[52] U.S. Cl. ..................................... 179/1 N; 73/585; 128/746
[58] Field of Search ........................ 179/1 N, 175.1 A; 128/746; 73/585

[56] References Cited

U.S. PATENT DOCUMENTS

| | | | |
|---|---|---|---|
| 3,222,456 | 12/1965 | Hyman | 179/1 N |
| 3,784,750 | 1/1974 | Stearns et al. | 179/1 N |
| 3,793,485 | 2/1974 | Feezor et al. | 179/1 N |
| 3,906,158 | 9/1975 | Lake | 179/1 N |
| 4,224,468 | 9/1980 | Calder, Jr. | 179/1 N |

FOREIGN PATENT DOCUMENTS 733655  5/1980  U.S.S.R. ............................. 128/746

OTHER PUBLICATIONS von E. Zwicker "Mithörschwellen-Periodenmuster amplitudenmodulierter Töne" Acustica, vol. 36, (1976/77), pp. 113-120.

Primary Examiner—G. Z. Rubinson
Assistant Examiner—Keith E. George
Attorney, Agent, or Firm—Hill, Van Santen, Steadman, Chiara & Simpson

[57] ABSTRACT

In an exemplary embodiment, for testing the chronological resolution of hearing, acoustic signals are supplied to the ear to be tested via an earpiece and consist of a test tone which can be interrupted and of a masking sound which can be modulated, their frequency and amplitude level being adjustable. Complicated measures are necessary for the measurement of the so-called listening threshold period pattern in order to present a complete pattern for identifying the chronological resolution of the hearing. In contrast, the disclosure provides an uncomplicated measuring device which is also easy to operate and with which the maximum and the minimum of the listening threshold period pattern or, respectively, their difference can be determined. To this end, the disclosure provides a device with channels generating respective sound signals, each of the channels having its own generator. Whereas the first generator is designed in the manner standard given electro-acoustical audiometers, that for the second channel has a noise generator whose output is modified by means of frequency band selection filters to provide a noise band with a mean frequency which can be matched to changes in the selected frequency of the first channel, and whose output amplitude level can be increased to a suitable value in comparison to the quiescent hearing threshold level (RHS) of the test tone. The disclosed device is particularly suitable for use in testing hearing.

17 Claims, 7 Drawing Figures

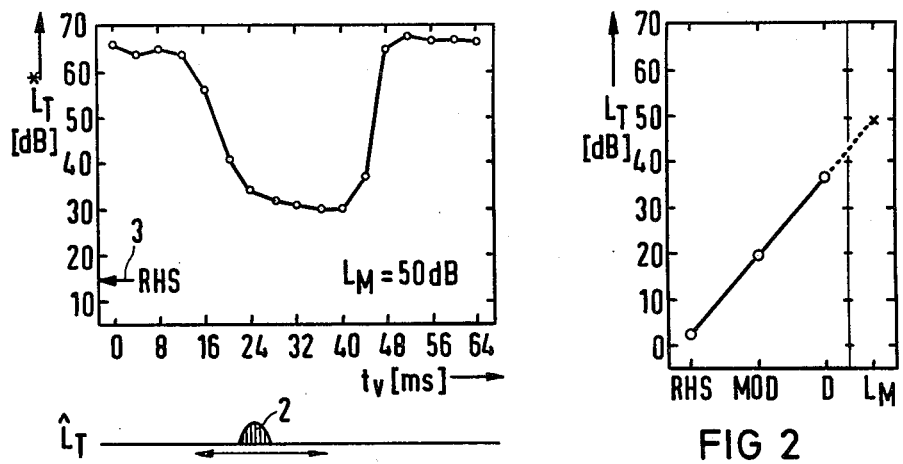
FIG 1
FIG 2
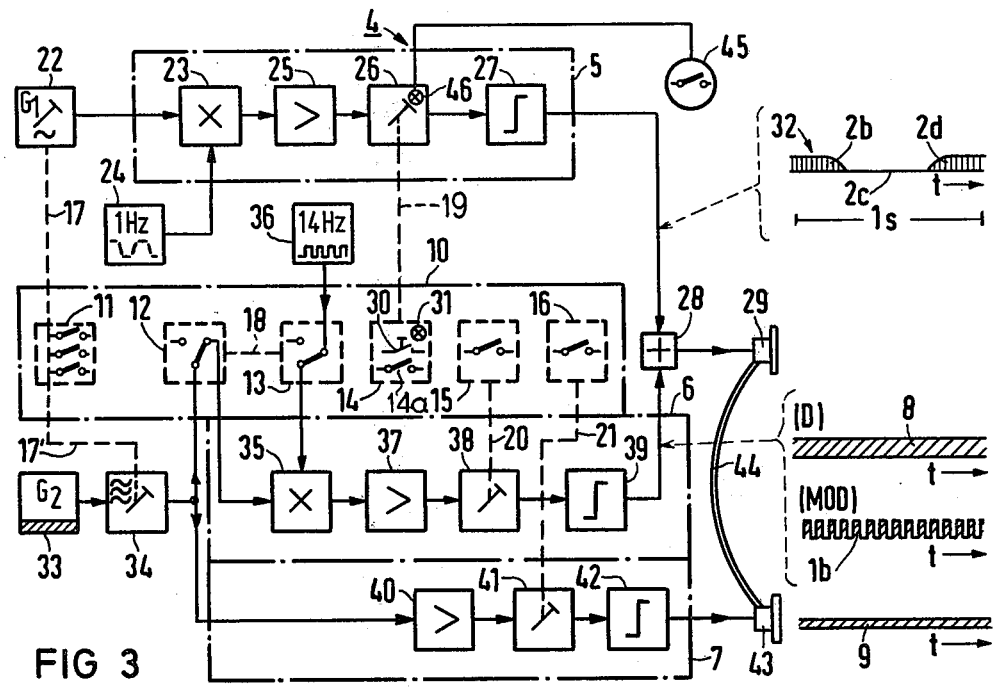
FIG 3

ELECTRO-ACOUSTICAL MEASURING DEVICE AND METHOD

BACKGROUND OF THE INVENTION

The invention relates to an electro-acoustical measuring device for testing the chronological resolution of hearing by means of acoustic signals to be supplied to the ear under examination via an earpiece, said acoustic signals consisting of a continuous test tone which can be interrupted and masking sound which can be pulse-modulated and whose pitch and level can be separately adjusted. A device of this type is known, for example, from "ACUSTICA", Vol. 36 (1976/77), Pages 113 through 120, particularly FIG. 1.

In addition to the frequency resolution of hearing which can be determined in a simple manner with audiometers, its chronological resolution in the acceptance of information, particularly in that of speech, also plays a very important role. If, after loud vowels, the hearing does not become sensitive quickly enough that it can also perceive following, soft consonants, the speech is not understood. This effect is also noticeable given persons with normal hearing when a speaker speaks quickly in a very reverberant space (for example, announcements at railroad stations which are often completely incomprehensible). The soft consonants which, however, are very important for the information contained in speech are then covered by the reverberant, loud vowels.

The chronological resolution of hearing can be described by means of simultaneous, pre- and post-masking. The combination proceeding from the effects of these maskings is measured in the so-called listening threshold period patterns of periodically amplitude-modulated maskers, as is treated in the reference cited in the above introductory paragraph. Thereby, a rectangular modulation is periodically undertaken with a modulation frequency of, for example, 15.6 Hz. The period of this masking sound then amounts to 64 ms (32 ms on and 32 ms off). A short test tone pulse, for example 4 ms long, is respectively offered within this period at a specific point in time (variable from measuring point to measuring point). Since the periods repeat with 15.6 Hz, the test sound is a pulse sequence of acoustical pulses of the repetition rate of 15.6 Hz. Masking sound and test sound are chronologically synchronized: in order to identify the listening threshold period pattern, the listening threshold of the test sound is measured as a function of the chronological shift of the test sound within one period of the masking sound.

The result of such a measurement upon employment of a device according to the present invention is illustrated in FIG. 1 for a masking octave noise of the mean frequency 1.5 kHz (completely rectangularly modulated with 15.6 Hz in its amplitude). The test tone frequency amounts to 1.5 kHz; the test tone duration amounts to 4 ms given 2 ms rise and decay time. The level $L_T^*$, from which the barely perceptible test tone pulse $L_T$ was excerpted, is illustrated as a function of the delay time $t_v$ within a period of the masking sound. In order to be able to identify the investigated interrelationship with sufficient precision, sixteen measuring points within the period of 32 ms were selected. In FIG. 1, a period of the masking sound 1, 1a (oblique shading) as well as a test pulse 2 (vertical shading) are illustrated below the abscissa. The level $L_M$ of the octave noise, from which the masking sound 1, 1a was excerpted, amounts to 50 dB. The listening threshold period pattern reveals high listening thresholds in those parts of the period in which the masking sound is switched on. After the masking sound 1 is switched off, the listening threshold sinks more slowly (post-masking), then it increases again before the masking noise 1a is again switched on (pre-masking). The quiescent hearing threshold (RHS), which is indicated by means of an arrow 3 at the ordinate, is not reached during the pause lying between 1 and 1a. On the contrary, the minimum of the listening threshold period pattern, given the parameters selected, lies somewhat below the mean between the maximum and the quiescent hearing threshold (RHS).

SUMMARY OF THE INVENTION

The invention proceeds from the perception that the course of the listening threshold period pattern in detail is less decisive for characterizing the chronological resolution than is, on the contrary, the difference between the maximum and the minimum in comparison to the value of the quiescent hearing threshold (RHS). It therefore takes as its object to avoid the known, complicated device for recording a complete pattern in the psychoacoustical measuring technique and to specify an uncomplicated measuring device which is likewise easy to operate and in which the maximum and the minimum or, respectively, their difference can be identified. Given an electro-acoustic measuring device according to the generic part of claim 1, this object is achieved by means of the features specified in the characterizing part of said claim. Expedient developments of the invention are the subject matter of the subclaims.

A possibility for the solution is to identify only the two values at $t_v = 0$ and at $t_v = 32$ ms determinate for the extremes instead of the sixteen points of the overall listening threshold period pattern. However, one dare not assume that the minimum always lies precisely in the center of the pause, as can be derived from the reference cited above (next to the last line, paragraph one of the specification introduction). Often, the minimum shifts toward greater delay times.

It would therefore be even more favorable if the minimum could be measured with a continuous test tone. This would be admissible in case a shift of the listening threshold toward smaller levels as a result of the integration properties of hearing could be taken into consideration. This would easily be possible if the maximum were likewise identified with a continuous test tone because only the difference between the maximum and minimum is then important. As experiments which led to the invention demonstrated, the maximum can be identified with a continuous test tone when the pause in the amplitude-modulated, masking octave noise is switched off and the masking noise, like the test sound, is offered as a continuous sound.

Such a method would also have the additional, great advantage that the patient would always have the same test tone to take into consideration. Without losing its effect as a continuous tone for the measurement, said test tone is expediently offered interrupted with respect to frequency and level (for example, 500 ms on, 500 ms off) because identification is then easier. With this test tone which is very slowly modulated, i.e., interrupted, in comparison to the pulse-modulated masking tone, there are then measured (a) the quiescent hearing threshold (RHS), (b) the listening threshold (D) given a masking octave continuous noise whose level is selected in such manner that the listening threshold lies approximately 30 dB above the RHS, and (c) the listening threshold (MOD) given masking, amplitude-modulated octave noise. Proceeding from three continuous test tone sound measurements which can also be executed by untrained personnel, there thus derive, in addition to the quiescent hearing threshold (RHS), two further measured values (D and MOD) which exhibit a close relationship to the maximum and to the minimum of the listening threshold period pattern and thus, are characteristic for the chronological resolution of hearing.

In the following, further details and advantages of the invention are explained on the basis of the exemplary embodiments illustrated in the Figures of the accompanying sheets of drawings; and other objects, features and advantages will be apparent from this detailed disclosure and from the appended claims.

BRIEF DESCRIPTION OF THE DRAWINGS

In FIG. 1 the listening threshold period pattern covered by 4 ms long 1.5 kHz acoustical pulses due to octave noise at 1.5 kHz mean frequency and a level of 50 dB is illustrated, being rectangularly modulated with 15.6 Hz;

In FIG. 2 is illustrated in a diagram, the listening thresholds—identified under the conditions of FIG. 1—of continuous tones, covered by continuous noise (D) and by modulated noise (MOD), as well as the quiescent hearing threshold (RHS);

In FIG. 3 is shown a block diagram of a device and the time functions of sound levels which can be attained therewith;

DETAILED DESCRIPTION

Figure 4:
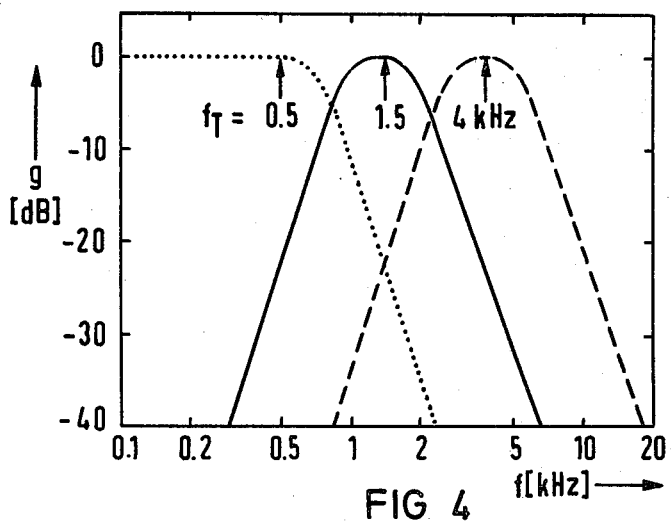
In FIG. 4 is illustrated in a diagram, the frequency dependency of the gain g of the filters employed for the production of the band-limited noise.

The description of FIG. 1 under the heading "Background of the Invention" is incorporated as part of this detailed description.

If the three measured values RHS, D, MOD for persons with normal hearing, as indicated in FIG. 2, are to lie on a straight line when they are entered at equal horizontal distances from one another, and moreover, if the measurement is to be carried out at the three frequency values, then the following determination of the variables is expedient from the point of view of as gap-free as possible as coverage of all possible hearing faults and a simple, graphical presentation:

Test Sound (Channel 5, FIG. 3)

Interrupted continuous tones (500 ms on, 500 ms off, =1 Hz, at frequencies of 500 Hz, 1500 Hz and 4000 Hz, adjustable in 5 dB steps for sound pressure levels between −5 dB and +115 dB. In addition, a drop or, respectively, boost of the values attainable in the 5 dB steps by 2.5 db can be provided, for a more precise identification of the threshold.

Masking Sound (Channel 6, FIG. 3)

A generator is first to be provided for the masking sound for octave-wide continuous noise for identifying the listening threshold D given masking continuous noise, said generator being provided for generating noise bands with the mean frequencies of 500 Hz, 1500 Hz and 4000 Hz whose levels can be adjusted in 10 dB steps for sound pressure levels between 0 dB and 100 dB as continuous sound. The same noise is to be provided for identifying the MOD, however, an additional modulator is to be provided for the rectangular amplitude modulation with 14 Hz, so that periods of 72 ms and pauses of 36 ms arise.

Appertaining time functions $2b$, $2c$, $2d$, 8, $1b$, and 9 are illustrated in FIG. 3 at the side of the block diagram of the device 4 and to the right of the three channels, i.e., the test tone channel 5, the masking sound channel 6 and the isolating (opposite ear deafening) sound channel 7. The device 4 contains a control panel 10 with keys 11 through 16 and appertaining displays of the values set which are known in audiometry per se and which are not separately illustrated for the sake of clarity. Insofar as required for an understanding of the invention, the controls between the elements of the control panel 10 and the channels 5 through 7 are indicated with broken lines 17 through 21 in FIG. 3.

The test sound is generated in channel 5 proceeding from an acoustic generator 22. Three frequencies (500 Hz, 1500 Hz and 4000 Hz) can be set by selector 11. In order to avoid the danger of a falsification of the measurement due to the consideration of distortion products, the k-factors are smaller than 0.1%. The following modulator 23, which is controlled by a generator 24, sees to it that the test tone is "softly" interrupted (approximately 20 ms transition time) with a frequency of approximately 1 Hz. The interrupted tone is amplified in an amplifier 25 and is supplied to one of the two head set ear pieces 29 via a divider 26, an audiometer distortion corrector 27 (cf. German LP No. 2,855,794) and via a summation point 28. The divider 26 is controlled proceeding from the keyboard 10 as indicated by coupling line 19 so that the level rises or, respectively, decreases by 5 dB, for instance, each time key 14 (controlling the lower contact $14a$) is actuated (pressed). The sound pressure level $L_T$ is displayed by means of luminescent diodes in the manner known per se in audiometers and can be adjusted between −5 dB and +115 dB. The test tone level $L_T$ can be reduced by 2.5 dB by means of pressing an additional key 30, whereby a display light 31 flashes. The time function of the test sound, which is identical for all three measurements, is illustrated to the right next to the channel 5 and is referenced with 32. In the illustrated waveform section of one second length, the waveform exhibits a runout part $2b$, a pause $2c$ and a beginning part $2d$.

The masking sound of channel 6 is generated in a generator 33 for white noise. A low-pass filter 34, or one of the octave band passes to be incorporated at the same location (said octave band passes not being separately illustrated), are post-connected to the generator 33. The commutation of the filters, whose gain g is illustrated in FIG. 4 as a function of the frequency f, is coupled to the commutation of the test tone frequency selector in 11 via 17'.

The band widths and the attenuation edges of the filters are selected in such manner that, on the one hand disruptive transit times of the operating mode MOD which might occur as a result of the phase response of the filters are avoided, but, on the other hand, the volume level $L_M$ of the masking noise is considerably reduced in comparison to that of the white noise of the generator 33 so that the hearing is not more greatly stressed than is absolutely necessary for the measurement. Given a highly frequency-dependent hearing loss, this is particularly pleasant for patients, because a particularly great overall loudness is otherwise generated in case of a broad-band masking. The octave band pass can be replaced by a low-pass filter 34 for the low frequency position ($f_T$=500 Hz).

For measuring the quiescent hearing threshold RHS, the noise in the channel 6 remains switched off by means of employing the key 12 (placing the contact of key 12 in its left hand position). The output of the filter 34 is only relayed to the modulator 35 for measuring the listening thresholds D or, respectively, MOD. The modulator 35 is connected to the 14 Hz rectangular generator 36 for the operating mode modulation MOD (the lower position shown for the contact of key 13), so that the masking noise is completely modulated in its amplitude (waveform 1b). Rectangular amplitude modulation is employed because the results can be more easily interpreted. Modulation with 14 Hz has proven itself. Given the selected parameters, values of D, MOD, RHS which lie on a straight line (FIG. 2) then derive for normal hearing. Other modulation frequencies would also be possible if one takes into consideration that the effect to be investigated does not exclusively occur at 14 Hz but, rather, also at higher and lower frequencies. Such values as lie between 4 Hz and 100 Hz prove favorable because of the pre-masking and the post-masking in hearing.

The 14 Hz generator 36 is disconnected from the modulator 35 for the operating mode continuous noise D (upper position of the contact of key 13), so that uninfluenced continuous noise arises. The masking sound for D or MOD arrives at the same head set earpiece 29 as the test sound from the channel 5 via an amplifier 37, divider 38, audiometer distortion corrector 39 and the summation point 28. The divider 38 controlled by means of pressing the key 15 is provided, just like the divider 26, with a display known from audiometry and allows sound pressure levels between 0 dB and 110 dB to be set in 10 dB steps for the masking noise. The time functions of the masking sound levels arising in channel 6 are illustrated at the right next to the channel 6 for continuous noise D and modulated noise MOD and are referenced with 8 and 1b.

As isolating noise, the continuous noise at the generator 33 (which is applied to the test tone frequency from the generator 22 of channel 5) can also be employed in the third channel referenced with 7, said continuous noise being tapped at the output of the filter 34. It arrives at the other earpiece 43 of a head set exhibiting a head strap 44 via an amplifier 40, a divider 41 and a distortion corrector 42. The level $L_V$ of the isolating noise can be varied in 10 dB steps between 20 dB and 80 dB by pressing the key 16. This suffices because with key 16 the selected adjustment of the parameters can provide sufficent isolation (can be sufficently deafening) in all cases. The level $L_V$ respectively achieved can likewise be displayed in a manner standard in audiometers by means of luminescent diodes.

The three measurements for producing diagrams (straight lines) according to FIG. 2 are expediently carried out in the device in the below sequence at the respectively selected frequency because of the increasing degree of difficulty in the sequence RHS, D and MOD:

1. RHS Identification of the quiescent hearing threshold of the interrupted continuous tone 32, FIG. 3.

2. D Identification of the listening threshold of the same tone 32, masked by the continuous octave (low-pass) noise 8, FIG. 3, with a level ($L_M$) that lies approximately 40 dB above the level of the RHS. Increasing the level ($L_M$) by approximately 40 dB has proven favorable. When the hearing loss is greater than, for example 60 dB, 30 dB can also suffice for the masking level $L_M$.

3. MOD Identification of the listening threshold of the same tone 32, FIG. 3, masked by the same noise which, however, is rectangularly amplitude-modulated with 14 Hz (waveform 1b). This value (for MOD), which has proven expedient in view of a simple presentation of the measured results because of the masking properties of hearing, lies rather precisely between the values for RHS and D for persons with normal hearing.

In the implementation of the tests, the test tone frequency $f_T$ of the operating mode RHS and a level $L_T$ of the interrupted test tone (waveform 32) which is audible for the test subject (VP) is first selected. The VP is informed that he is to pay attention only to this test sound (waveform 32) during all measurements and is to indicate by means of a press button 45 known from audiometry that he hears the interrupted test tone. Pressing this button triggers a signal at the display of the person conducting the test in that, for example, a lamp 46 is illuminated. With this display, which was achieved by changing the level $L_T$ of the test tone in 5 dB or, respectively, 2.5 dB steps, the person conducting the test identifies the quiescent hearing threshold RHS and marks the value in the diagram (FIG. 2), for example, by means of a small circle.

The listening threshold is now identified in the same manner in the operating mode continuous D. The level $L_M$ (FIG. 2) of the masking noise (waveform 8, FIG. 3), to that end, is selected approximately 40 dB above the quiescent hearing threshold level RHS. For the purpose of documentation, this value $L_M$ is likewise marked in the diagram (FIG. 2) at the provided location with a cross; and the listening threshold D is measured, as described above for RHS, and is entered at the location of the diagram provided for that purpose. Finally, without altering the level $L_M$ of the masking noise, the listening threshold of the operating mode modulation MOD is identified as the last measurement. The value lies between those for RHS and D, nearly in the exact center between both for persons with normal hearing. The two latter listening thresholds D and MOD are likewise entered as circles in the diagram (FIG. 2), so that, as proceeds from FIG. 2, a straight line placed through the measured points for RHS, MOD and D arises as a record.

Figure 5:
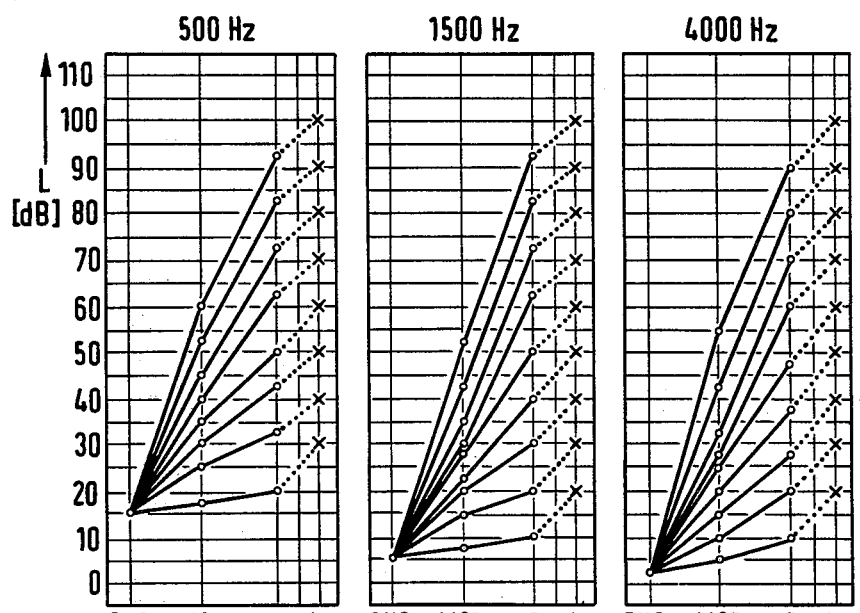
In FIG. 5 is illustrated in diagrams, listening thresholds (D, MOD, RHS) connected to "chronological resolution lines" at frequencies of 500 Hz, 1500 Hz and 4000 Hz and different levels of the masking noise.

As an example for the dependence of the measure results on the level $L_M$ of the masking noise, the records of a VP with normal hearing are illustrated in FIG. 5 at the three said frequencies 500 Hz, 1500 Hz and 4000 Hz and upon employment of levels $L_M$ between 20 and 100 dB with respective 10 dB spacing. They show that the listening thresholds D increase to the same degree as the levels $L_M$ of the noise. Thereby, the level $L_M$ lies approximately 10 dB above the listening threshold.

The listening thresholds MOD for modulated noise, independently of the level $L_M$, lie approximately in the center between the values for D and RHS, so that the connection of the measured values indicated as circles produces a bundling of straight lines with different slopes which proceed from the point RHS.

It can be derived therefrom that prescribing the value of the masking noise $L_M$ is not critical. On the contrary, it can be selected in such manner that, even given damaged hearing, the VP does not find the masking noise too loud and that, nonetheless, a boost from the quiescent hearing threshold RHS to the listening threshold D of approximately 30 dB is achieved with the presence of continuous noise. This is produced given a level $L_M$ which lies approximately 40 dB above the quiescent hearing threshold RHS.

For a person with normal hearing, i.e., for a VP with normal chronological resolution of hearing, the measured values in FIG. 2 are in a diagram with markings for RHS, MOD and D entered at equal distances on the abscissa and for the magnitudes (decibels) in the ordinate. The three measured values for RHS, MOD and D found under the said boundary conditions and entered as circles then lie rather well on a straight line, whereby fluctuations of only ±2.5 dB occur. This form of the position of the measured values allows a simple test of the functionability of hearing with respect to the chronological resolution.

Figure 6:
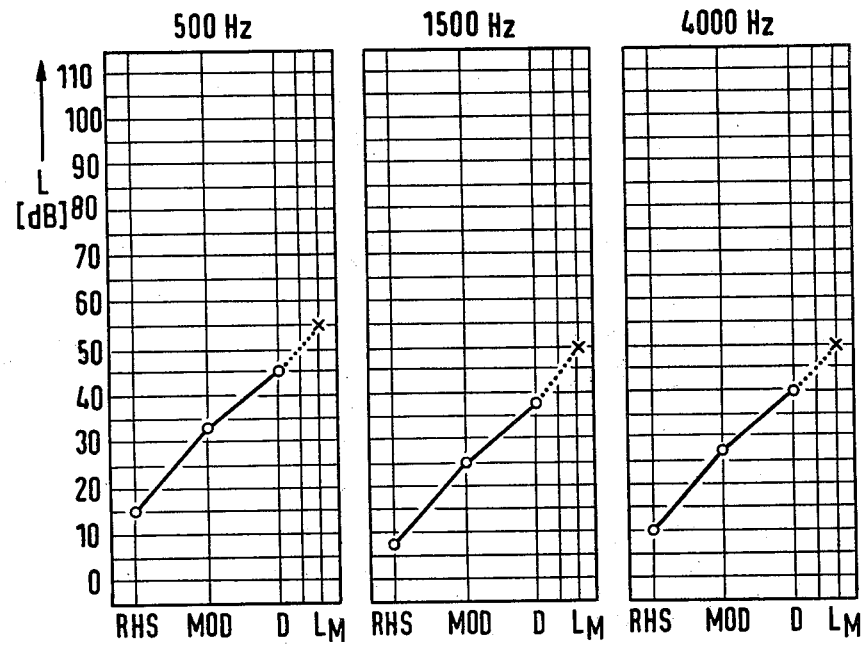
In FIG. 6 is shown an indication coinciding with FIG. 5 of the mean values of measurement of sixteen test subject at 500 Hz, 1500 Hz and 4000 Hz and a masking noise ($L_M$) of 40 dB above RHS; and In FIG. 7 there is presented an indication of measurements for a test subject with a hearing loss of approximately 50 dB at frequencies around 4000 Hz under conditions which otherwise coincide with those of FIG. 6.

Median values and probably fluctuations of the measured values of sixteen VP's with normal hearing are entered in FIG. 6; the boundary values thereby observed are $L_M$ at 40 dB±5 dB above the RHS. These data show how slight the deviations remain even after averaging, into which there enters that, although the RHS is precisely measured at 2.5 dB, the level $L_M$ nonetheless can only be precisely adjusted to within 5 dB. The individual deviation of the value MOD from the precise median value (D+RHS)/2 produced an average of 2.5 dB±2.5 dB at 500 Hz, 0 dB±1.25 dB at 1500 Hz and 2.5 dB±2.5 dB at 4000 Hz. It can therefore be derived therefrom that the description "when the data entered in the record as circles lie on a straight line, this corresponds to normal chronological resolution of hearing" is very well met.

Figure 7:
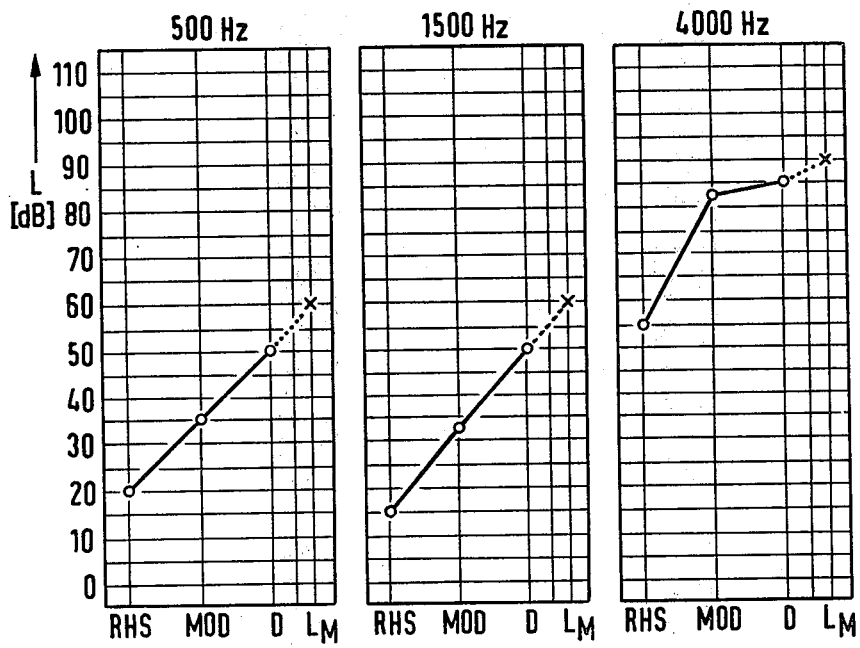

As an example for an abnormal chronological resolution at high frequencies, the record of a VP with a hearing loss of approximately 45 dB at frequencies above 3 kHz is reproduced in FIG. 7. It shows normal behavior at 500 and at 1500 Hz at which, of course, no hearing loss exists. At the high frequency of 4000 Hz, however, an abnormal course of the diagram obtained occurs. There, not only is the quiescent hearing threshold RHS boosted but, rather, the listening threshold MOD is also clearly boosted above the connecting line between RHS and D. It lies only a few decibels below the value for D. In the listening threshold period pattern of the known type (FIG. 1), this would only correspond to a very slight dip during the pause between 1 and 1a in which no noise is offered. The method of measuring the listening thresholds of test tones which is executed by means of octave continuous noise and amplitude-modulated noise according to the invention produces the same statement in a much simpler manner.

It will be apparent that many modifications and variations may be effected without departing from the scope of the novel concepts and teachings of the present invention.

I claim as my invention:

1. An electro-acoustical device for use in determining the chronological resolution of hearing of an individual, said device comprising earphone means which may be applied to one ear of an individual being tested, a test tone channel connected with said earphone means for producing a test tone at the earphone means which can be interrupted, a masking sound channel which can be connected with the earphone means, and operable during testing of an individual for producing a masking sound for association with the test tone at said earphone means, adjustment means in said channels for adjusting the frequency of the test tone, and the level of the test tone and of masking sound, wherein the improvement comprises: said masking sound channel having noise generator means for generating the masking sound and for supplying noise bands matchable in terms of their frequency band to the adjusted frequency of the test tone, said adjustment means being operable for boosting the level of the masking sound in comparison to the quiescent hearing threshold level of the test tone, and a pulse modulator selectively operable in said masking sound channel for modulating the amplitude of said masking sound, while being switchable to an inactive condition to provide for the supply of a continuous unmodulated masking sound.

2. A device according to claim 1, with said noise generator means comprising band selection filters for matching the mean frequency of the noise bands to the frequency of the test tone, said adjustment means being operable for boosting the level of the masking sound by ten through one hundred decibels in comparison to the quiescent hearing threshold level of the test tone and said pulse modulator providing for a modulation envelope with a modulation frequency in the range from about five Hz through about one hundred Hz.

3. A device according to claim 2, with said band selection filters comprising octave band pass filters and a low-pass filter (FIG. 4).

4. A device according to claim 1, with said noise generator means comprising a noise generator for white noise.

5. A device according to claim 1, with a head set having first and second earpieces and a head strap uniting said ear pieces, an isolating sound channel having means for connection to the second earpiece and means for coupling the test tone channel and the masking sound channel with the first earpiece.

6. A device according to claim 1, with said adjustment means in said test tone channel being operable to selectively supply one of a plurality of test tone frequencies which lie in the range from about 250 through 6000 Hz.

7. A device according to claim 1, with said test tone channel having a cyclically operable interrupter which alternately switches the test tone on for about 500 ms and off for about 500 ms.

8. A device according to claim 1, with said adjustment means in said test tone channel being operable for selectively supplying a test tone frequency which is switchable to about 500 Hz, to about 1500 Hz and to about 4000 Hz.

9. A device according to claim 1, with the adjustment means in said channels comprising switchable amplitude level adjusters for the step-wise change of the sound pressure level supplied by said channels.

10. A device according to claim 9, with one of the said level adjusters in said test tone channel being switchable in steps of 2.5 through 10 dB in the range from −5 through 115 dB.

11. A device according to claim 9, with said adjustment means comprising an auxiliary amplitude level adjuster in the test tone channel for the selective modification of the sound pressure level to a value which is intermediate the step-wise values provided by the switchable amplitude level adjuster in said test tone channel.

12. A device according to claim 11, with said switchable amplitude level adjuster in the test tone channel providing for step-wise change of the sound pressure level in steps of about five dB, and said auxiliary amplitude level adjuster providing a selective modification of about 2.5 dB.

13. A device according to claim 1, with an isolating sound channel and the masking sound channel having level adjusters switchable in ten decibel steps between 20 dB and 80 dB, and between zero dB and 100 dB, respectively.

14. A device according to claim 1, with means for selectively providing an amplitude modulation with a modulation frequency of about fourteen Hz in the masking sound channel so that masking sound intervals of about 72 ms and pauses of approximately 36 ms arise.

15. A device according to claim 1, with a variable frequency pulse modulator for selectively effecting amplitude modulation of the masking sound supplied by said masking sound channel at respective different modulation frequencies.

16. A device according to claim 1, with said test one channel being operable to selectively supply one of a plurality of tone frequencies which lie in a frequency range from about 500 Hz to about 4000 Hz.

17. An electro-acoustical method for testing the chronological resolution of hearing, said method comprising:

in a first step supplying to an individual whose hearing is to be tested a test tone and determining the value of the threshold sound pressure level at which the individual is able to hear the test tone, so as to determine the quiescent hearing threshold level (RHS) of the individual for said test tone, in a second step, supplying to the individual the same test tone masked by a continuous noise having a limited frequency band matched to the frequency of the test tone, and determining the sound pressure level at which the individual hears the test tone, so as to determine the listening threshold level (D) for said test tone when masked by said continuous noise, in a third step supplying to the individual the same test tone masked by noise having said limited frequency band, but which noise is rectangularly amplitude modulated, and determining the sound pressure level at which the individual hears the test tone, so as to determine the listening threshold level (MOD) for said test tone when masked by said noise which is rectangularly amplitude modulated, and carrying out said first, second and third steps such that chronological resolution of hearing can be judged from a diagram in which the determined threshold levels (RHS, D and MOD) are vertically plotted at equal horizontal distances from one another.

* * * * *